(12) United States Patent
Colthurst (10) Patent No.: US 8,977,370 B2
(45) Date of Patent: Mar. 10, 2015

(54) TREATMENT PATCH ELECTRODE FOR APPLYING ELECTRICAL IMPULSES TO THE BODY OF A PATIENT

(76) Inventor: James Colthurst, Hungerford (GB)

( * ) Notice: Subject to any disclaimer, the term of this patent is extended or adjusted under 35 U.S.C. 154(b) by 211 days.

(21) Appl. No.: 13/576,112

(22) PCT Filed: Dec. 15, 2010

(86) PCT No.: PCT/GB2010/002280
§ 371 (c)(1),
(2), (4) Date: Sep. 28, 2012

(87) PCT Pub. No.: WO2011/092499
PCT Pub. Date: Aug. 4, 2011

(65) Prior Publication Data
US 2013/0046362 A1    Feb. 21, 2013

(30) Foreign Application Priority Data
Feb. 1, 2010 (GB) .................................. 1001631.9

(51) Int. Cl.
*A61N 1/00* (2006.01)
*A61N 1/32* (2006.01)
*A61N 1/04* (2006.01)

(52) U.S. Cl.
CPC ............... *A61N 1/32* (2013.01); *A61N 1/0468* (2013.01); *A61N 1/0492* (2013.01)
USPC .......................................... 607/152; 607/115

(58) Field of Classification Search
USPC ........................... 607/115, 145, 150, 151, 152
See application file for complete search history.

(56) References Cited

U.S. PATENT DOCUMENTS

| 3,386,445 A | 6/1968 | McDonald |
| 4,509,535 A | 4/1985 | Bryan |

(Continued)

FOREIGN PATENT DOCUMENTS

GB       2 414 407 B       4/2009

(Continued)

OTHER PUBLICATIONS

International Search Report and Written Opinion for parent application PCT/GB2010/002280, having a mailing date of Mar. 24, 2011.

(Continued)

*Primary Examiner* — Scott Getzow
(74) *Attorney, Agent, or Firm* — Andrus Intellectual Property Law, LLP (57) ABSTRACT

A handheld treatment device is for applying electrical impulses to a living body through the surface of the body, for treating a variety of clinical conditions. The device comprises first and second electrodes for contact with the skin; a waveform generator for repeatedly generating an AC waveform for applying electrical impulses through the electrodes to the skin; a detector for detecting changes in the skin impedance and for generating output signals representing the skin impedance; means responsive to the output signals from the detector for monitoring the responsivity of the skin; and indicator means for generating a first indication when a predetermined level of responsivity is reached and a second indication when a pre-determined treatment has been administered. The device is characterised by a treatment patch comprising a flexible sheet having on one surface said first and second electrodes separated by insulation; a pair of leads connected respectively to said first and second electrodes; and a connection arrangement attached to the first and second leads for connecting the electrodes with said waveform generator. Each electrode comprises at least one elongate strip, with the, or each, strip of the first electrode being separated from the, or each adjacent, strip of the second electrode by a, or a respective, line of said insulation.

11 Claims, 11 Drawing Sheets

(56) References Cited

U.S. PATENT DOCUMENTS

| | | | |
|---|---|---|---|
| 4,619,266 A | 10/1986 | Hodgson | |
| 5,318,514 A * | 6/1994 | Hofmann | 604/20 |
| 5,464,386 A | 11/1995 | Hofmann | |
| 5,496,363 A | 3/1996 | Burgio et al. | |
| 2004/0059387 A1 | 3/2004 | Yu | |
| 2008/0103550 A1 | 5/2008 | Wenzel et al. | |
| 2008/0281382 A1 * | 11/2008 | Colthurst | 607/62 |

FOREIGN PATENT DOCUMENTS

| | | |
|---|---|---|
| GB | 2 454 481 A | 5/2009 |
| JP | 08-066482 A | 3/1996 |
| WO | 99/26686 A1 | 6/1999 |
| WO | 2004/049937 A1 | 6/2004 |
| WO | 2005/023361 A2 | 3/2005 |
| WO | 2005/023361 A3 | 3/2005 |
| WO | 2005/118061 A1 | 12/2005 |
| WO | 2006001644 A1 | 1/2006 |

OTHER PUBLICATIONS

UK Search Report for priority application GB 1001631.9, having a mailing date of May 25, 2010.

* cited by examiner

TREATMENT PATCH ELECTRODE FOR APPLYING ELECTRICAL IMPULSES TO THE BODY OF A PATIENT

CROSS-REFERENCE TO RELATED APPLICATIONS

This application is the U.S. national stage application of International Application No. PCT/GB2010/002280, filed Dec. 15, 2010, which International application was published on Aug. 4, 2011 as International Publication No. WO 2011/092449 A1 in the English language and which application is incorporated herein by reference. The International application claims priority of Great Britain Patent Application No. 1001631.9, filed Feb. 1, 2010, which application is incorporated herein by reference.

BACKGROUND

This invention relates to a treatment patch electrode for applying electrical impulses to a surface area of a living body for treating a variety of clinical conditions.

Our earlier GB Patent No. 2 414 407 discloses a handheld treatment device including an electrode arrangement which makes physical contact with the skin for treatment purposes. A repeatedly generated AC waveform is supplied to the electrodes for electro-stimulation of the surface of the skin, and changes in the skin impedance are monitored for evaluating and controlling treatment.

According to this patent, a handheld treatment device for applying electrical impulses to a living body through the skin, for treating a variety of clinical conditions, comprises: a pair of electrodes for contact with the skin; a waveform generator for repeatedly generating an AC waveform for applying electrical impulses through the electrodes to the skin; a detector for detecting changes in the skin impedance and for generating output signals representing the skin impedance; means responsive to the output signals from the detector for monitoring the responsivity of the skin; and indicator means for generating a first indication when a predetermined level of responsivity is reached and a second indication when a predetermined treatment has been administered. The disclosure of this patent is incorporated herein by reference.

The handheld treatment device of GB Patent No. 2 414 407 has proved extremely effective in clinical trials for treating a wide variety of clinical conditions, including the treatment of skin disorders, the treatment of broken bones, and the treatment of various medical disorders and diseases. However, there are certain conditions where treatment using the device may be hindered or impeded by the presence of dressings, body support elements or layers, or medical apparatus, for example where the clinical condition being treated includes a wound or damaged skin tissue concealed under a dressing or a broken limb supported in a plaster of paris cast.

SUMMARY

Accordingly, the present invention seeks to provide an improvement to the above earlier treatment device, which improvement is extremely simple, effective and easy to use, and is more versatile than and may extend the treatment range of the earlier device for treating a wide range of clinical conditions.

The present invention also aims to demonstrate benefits in treatment without harmful side effects, by providing a body interface capable of applying electrical impulses of relatively high amplitude and short duration to the body surface of an animal or patient for stimulating repair processes within the body.

According to the present invention there is provided a treatment patch electrode for applying electrical impulses to the body of a patient, comprising a flexible sheet having on one surface first and second electrodes separated by insulation, a pair of leads connected respectively to the first and second electrodes and a connection arrangement attached to the first and second leads for connecting the electrodes with an electro-stimulation apparatus, wherein each electrode comprises at least one elongate strip, and wherein the, or each, strip of the first electrode is separated from the, or each adjacent, strip of the second electrode by a, or a respective, line of said insulation.

The treatment patch electrode of the present invention may be employed with other electro-stimulation apparatus, but preferably it is employed with the handheld treatment device of GB Patent No. 2 414 407.

Thus, in the preferred embodiment, the treatment device is a handheld battery powered device, in which the detection means generates output signals in the form of pulses whose duration represents the impedance of the associated surface area of the body; the monitoring means monitors the responsivity of said surface area by measuring the duration of each pulse; and the indicating means is arranged to generate each indication when t satisfies a predetermined function of t.

In this instance, the indicating means is conveniently arranged to generate the first indication when $t_2 = 4.087 \, t_1^{0.7131}$ and to generate the second indication when $dZ/dt = 0$.

In the treatment patch electrode according to the invention, the surface area of the first and second electrodes is preferably substantial in relation to the area of the said one surface of the flexible sheet in order to ensure a maximum area of electrode interface with the body of the patient. By forming the treatment patch electrode as a flexible sheet, the patch may readily be applied to and mould itself around the contours of the patient's body parts, which significantly enhances treatment. The patch may be left in place between treatments without adverse effect, and disposed of once treatment is complete. The result is a treatment device which is extremely simple and easy to employ, as well as being versatile and adaptable to a significant number of clinical and medical applications.

The treatment patch electrode according to the invention thus has a number of advantages, not the least of which are ease of use and versatility, as well as the fact that the production cost can be low while the efficacy promises to be high. Further, the inexpensive construction and disposable nature of the patch electrode renders it highly suitable for medical applications where risks of infection are high and a sterile environment is paramount.

A further aspect of the invention features a method of treating of a human or animal through the body surface by means of the present treatment patch electrode.

BRIEF DESCRIPTION OF THE DRAWINGS

The invention is described further, by way of example, with reference to the accompanying drawings, in which.

DETAILED DESCRIPTION OF THE DRAWINGS

Figure 1:
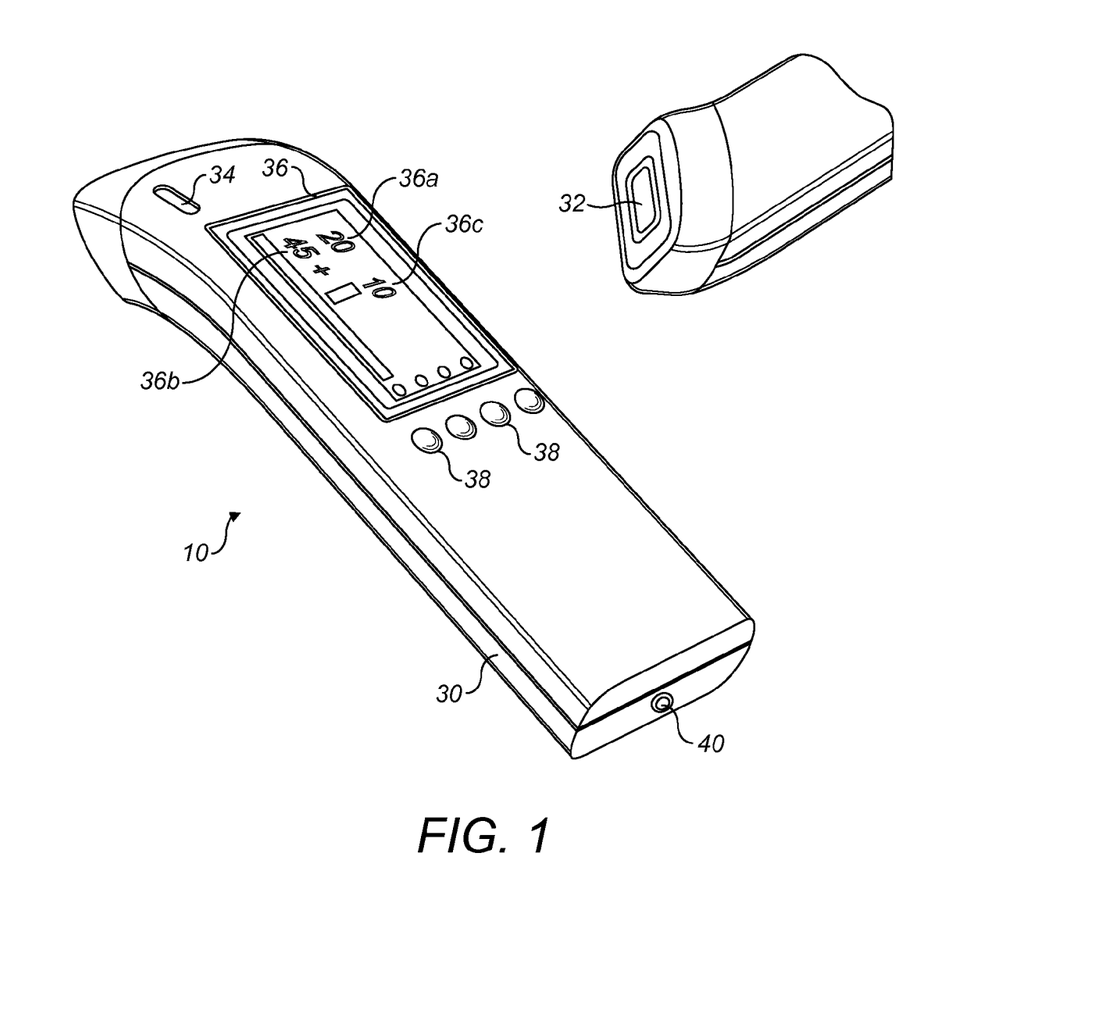
FIG. 1 is a perspective view of a handheld treatment device according to the present invention.

Referring initially to FIGS. 1 to 5, the present invention comprises a handheld treatment device 10 for applying electrical impulses to a human or animal body through a surface region of the body. For the purposes of the present description, the treatment of a human being will be described. The treatment device 10 is illustrated in FIG. 1 and is designed to be placed in contact with the skin or exposed surface of the body and to generate short AC electrical impulses for application to the body surface by way of electrodes, as described below.

The treatment device 10 comprises a body or housing 30 having a pair of electrodes 32 at one end and having on its back an on or off switch 34, a display 36 and a series of user control buttons 38. Four such buttons are shown in FIG. 1, but there may be any number depending on the number of different functions that may be controlled by the user. At the base of the treatment device, there is a socket 40 for receiving a plug of an additional plug-in element to be described below.

Figure 2:
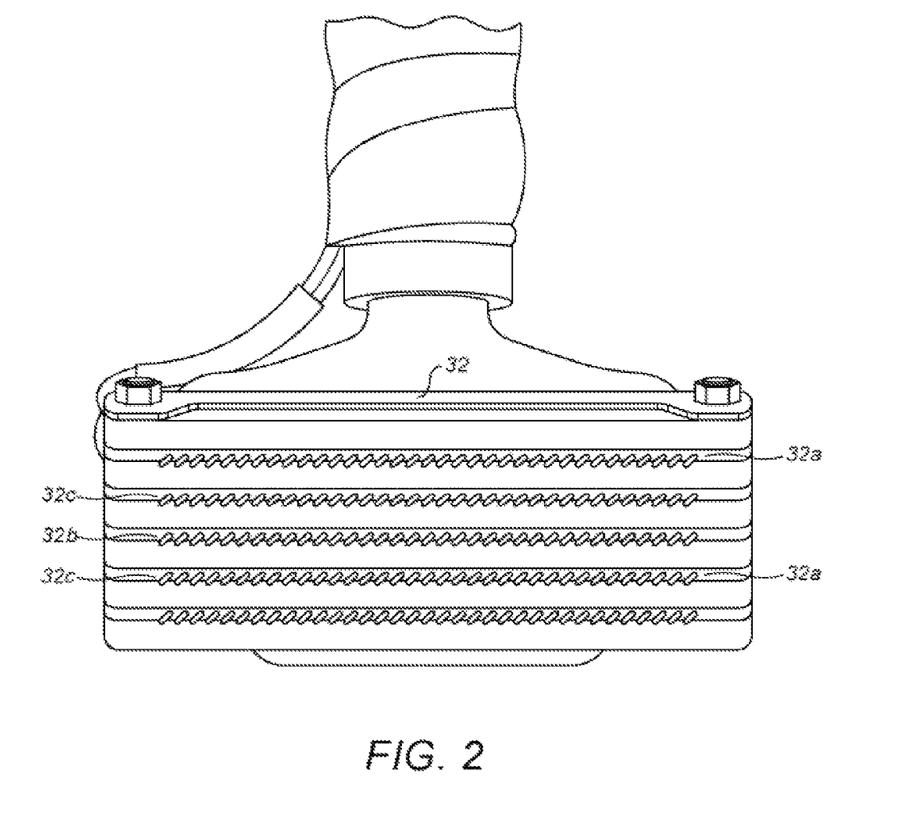
FIG. 2 is a diagram of the electrodes of the treatment device of FIG. 1.

The electrodes 32 have a very specific form designed primarily to ensure skin contact whether the skin is bare or is covered by hair or fur. More particularly, the electrodes are designed as a series of five parallel combs, in which the two outermost combs 32*a* constitute one electrode; the central comb 32*b* constitutes the other electrode, and the remaining two combs 32*c* flanking the central comb 32*b* are insulating elements. The electrodes 32*a* and 32*b* are therefore formed from a conductive material, while the combs 32*c* are formed from an insulating material. The dimensions of the combs are, however, identical, and each comb comprises a series of teeth arranged approximately 2.5 mm apart and having a length of approximately 2 mm.

Figure 3:
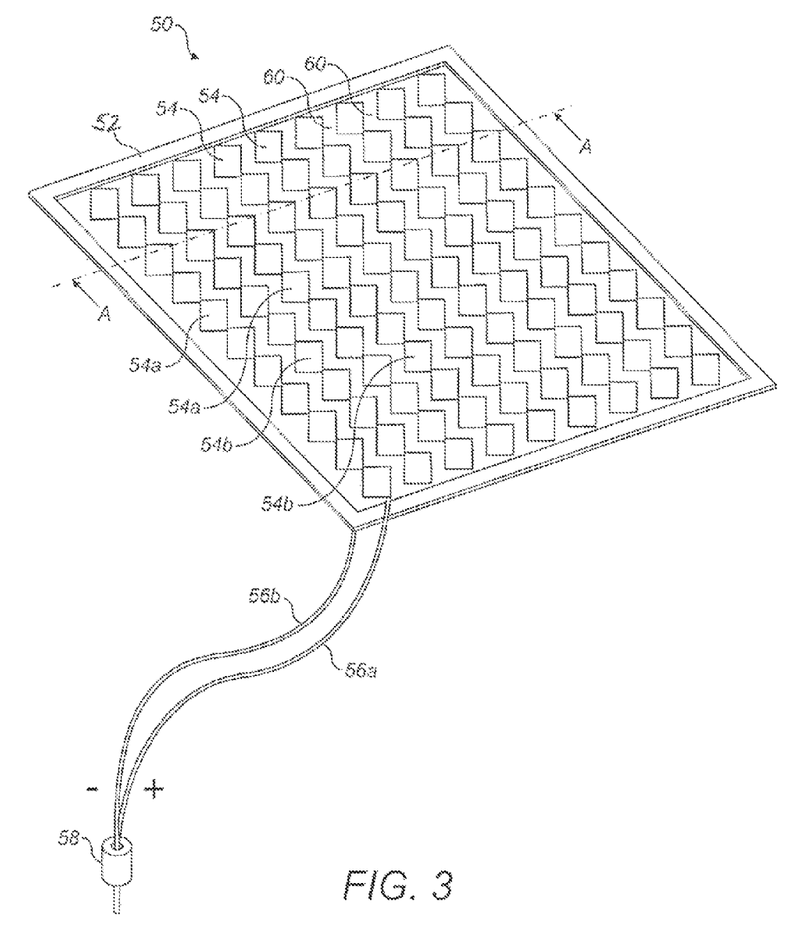
FIG. 3 is a perspective view of a treatment patch electrode according to the present invention.

Turning now to FIG. 3, an additional plug-in element for connection to the socket 40 of the handheld treatment device is shown. This additional plug-in element is a treatment patch electrode 50 according to the invention, comprising a flexible sheet 52 carrying on one surface a number of electrodes 54, which are connected by leads 56 to a plug 58 for insertion into the socket 40.

As shown in FIG. 3, the electrodes 54 are designed as a series of, eg nine, parallel strips, each separated by a line of insulation 60. The strips 54 comprise a first set of strips 54*a* forming a first electrode, alternating with a second set of strips 54*b* forming a second electrode. The strips 54*a* are all connected to one of the two leads 56, namely 56*a*, and the second set of strips 54*b* are connected to the other of the two leads 56, namely 56*b*, for connection to the housing 30 of the handheld treatment device 10. Each strip 54*a*, 54*b*, respectively, may take a variety of forms, but as shown here is formed as a series of overlapping rectangles or squares creating a long narrow band or strip electrode whose width alternately widens and narrows. Adjacent strips 54*a*, 54*b* are slightly offset longitudinally relative to one another so that their edges lie parallel and the insulation 60 between them constitutes a parallel sided zig-zag line.

Figure 4:
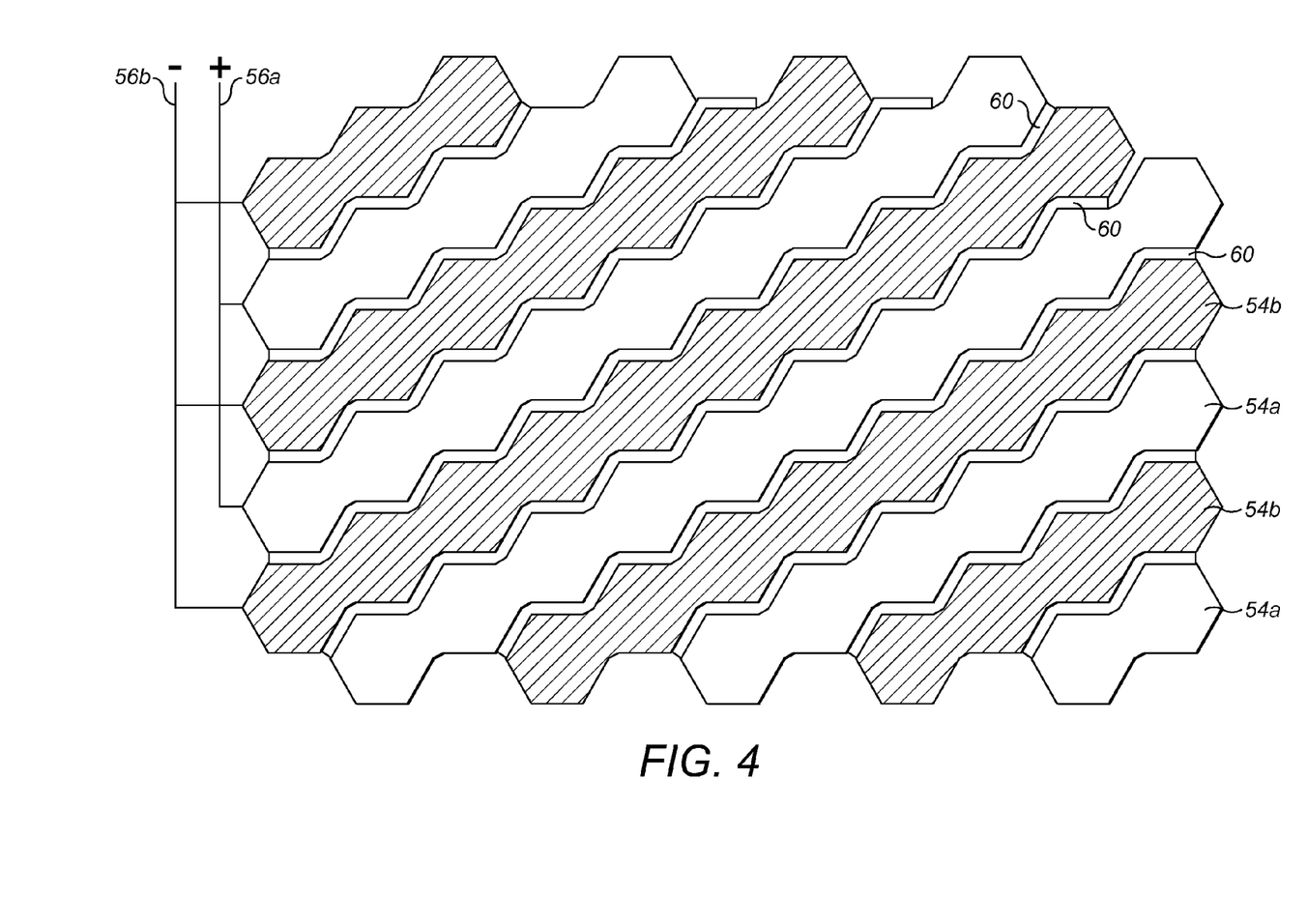
FIG. 4 is a diagrammatic enlarged view of a portion of a surface of the treatment patch electrode of FIG. 3.
Figure 5:
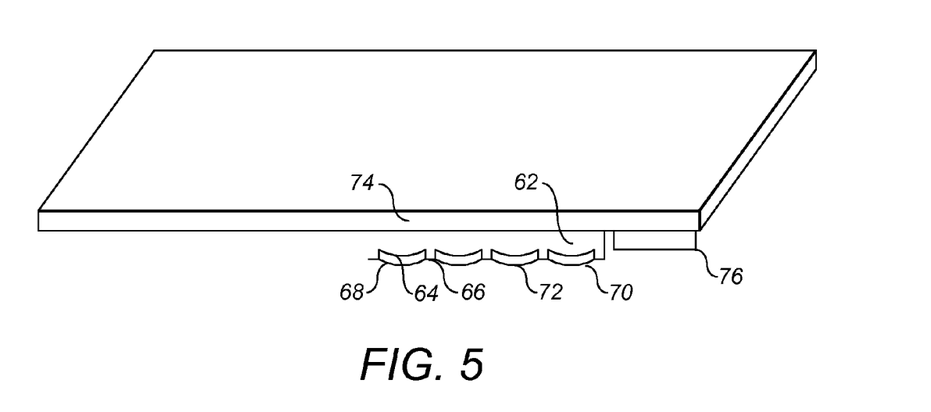
FIG. 5 is a sectional view through the treatment patch electrode of FIG. 3 along the line A-A.

The electrode formation is shown in greater detail in FIGS. 4 and 5, in which it can be seen that each electrode 54*a* and 54*b* comprises a continuous band of conductive material formed from a series of adjacent and joined hexagonal or honeycomb-shaped elements. In FIG. 3, each electrode appears as a conductive band formed from a series of overlapping rectangular elements, and in practice the degree of overlap may vary. The arrangement shown in FIGS. 4 and 5 is the result of a particular amount or degree of overlap. Between each band of conductive material, the lines of insulation 60 can be seen to be narrow zig-zag lines of constant width, such lines being narrower than the minimum width of the electrodes. This arrangement ensures a substantial area of electrode interface for treatment purposes, with adjacent electrodes having parallel edges and a constant narrow electrode spacing throughout the interface for effective signal generation between the electrodes.

In one embodiment of the treatment patch electrode according to the invention, shown in FIG. 5, the flexible sheet 52 comprises an insulating support layer 62, whose surface 64 is moulded to form narrow upstanding or raised walls 66 providing the insulating lines 60 and wider recessed surface regions 68 providing channels 70 for receiving conductive material 72 forming the electrodes 54. As indicated, each recessed surface region 68 has a curved contour in the lateral direction, and the depth of the recessing is sufficiently small that the conductive material 72 when applied projects well beyond the upper surfaces of the raised walls 66. In the longitudinal direction, the recessed surface regions 68 conform to the desired form of the electrodes 54, and each raised wall 66 bounding the adjacent recessed surface region 68 will conform to and trace the edge outline of the electrode 54 as shown in and described with reference to FIG. 4.

In the manufacturing process, the support backing 62 may be first formed, eg by standard moulding techniques, and then a conductive coating 72 may be deposited in each channel 70 to form the associated electrode strip 54. Since the sheet 52, and therefore the insulating support backing 62 is flexible, it follows that the electro-coating 72 is also flexible and therefore the sheet 52 can be applied to the body of a patient and moulded to the contours of the body parts with ease.

In a particular example of the design shown in FIG. 5, the support backing 62 may be formed from an insulating plastics material approximately 2-3 mm in depth, and the conductive coating 72 may be a thin metallic film deposited on the surface section 68 of the support backing 62.

FIG. 5 also shows a cover layer 74 formed across the surface of the support backing 62 opposite the electrode carrying surface, and this cover layer 74 may be formed with a peripheral adhesive strip 76 encircling the support backing 62 for affixing the treatment patch to a patient's body parts.

In practice, the cover layer 74 may alternatively be omitted and a conventional dressing may be applied over the basic flexible sheeet 52 of the treatment patch for retaining the treatment patch in situ.

Figure 6:
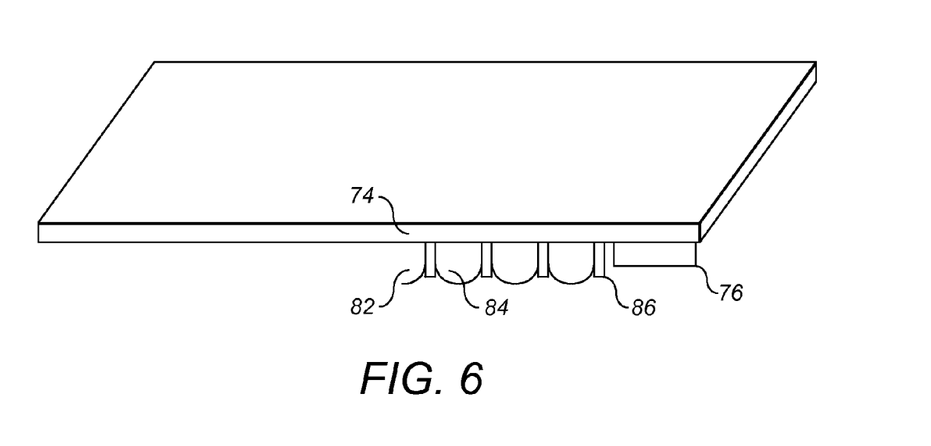
FIG. 6 is a sectional view similar to FIG. 5 but showing a modification of the treatment patch electrode.

FIG. 6 shows a modification of the arrangement of FIG. 5, in which the unitary support backing 62, carrying thin electrode strip coatings 72, is replaced by an arrangement which has a similar appearance from above but which is constructed differently. In the treatment patch electrode of FIG. 6, there is no support backing but the electrode strips and the lines of insulation themselves combine to form a flexible layer 82, in which each electrode strip 84 and each insulating strip 86 extend the full depth of the layer 82. To achieve this, the strips 84 and 86 may be adhesively joined together to form the alternating arrangement of electrodes 54 and lines of insulation 60 as shown in FIG. 3. As in the case of the FIG. 5 embodiment, each electrode strip 84 has a surface contour 88 that is curved in the lateral direction, and each insulating line 86 comprises a small upstanding wall 90 between the two adjacent electrode strips 84. However, in this instance, the approximate depth of each electrode strip 84 and of each insulating strip 86 may be expected to be of the order of 2-3 mm.

As in the case of the FIG. 5 embodiment, a cover layer 74 with a surrounding adhesive strip 76 may be provided for the FIG. 6 embodiment, or a conventional dressing may be employed in use to hold the patch electrode in place.

Figure 7:
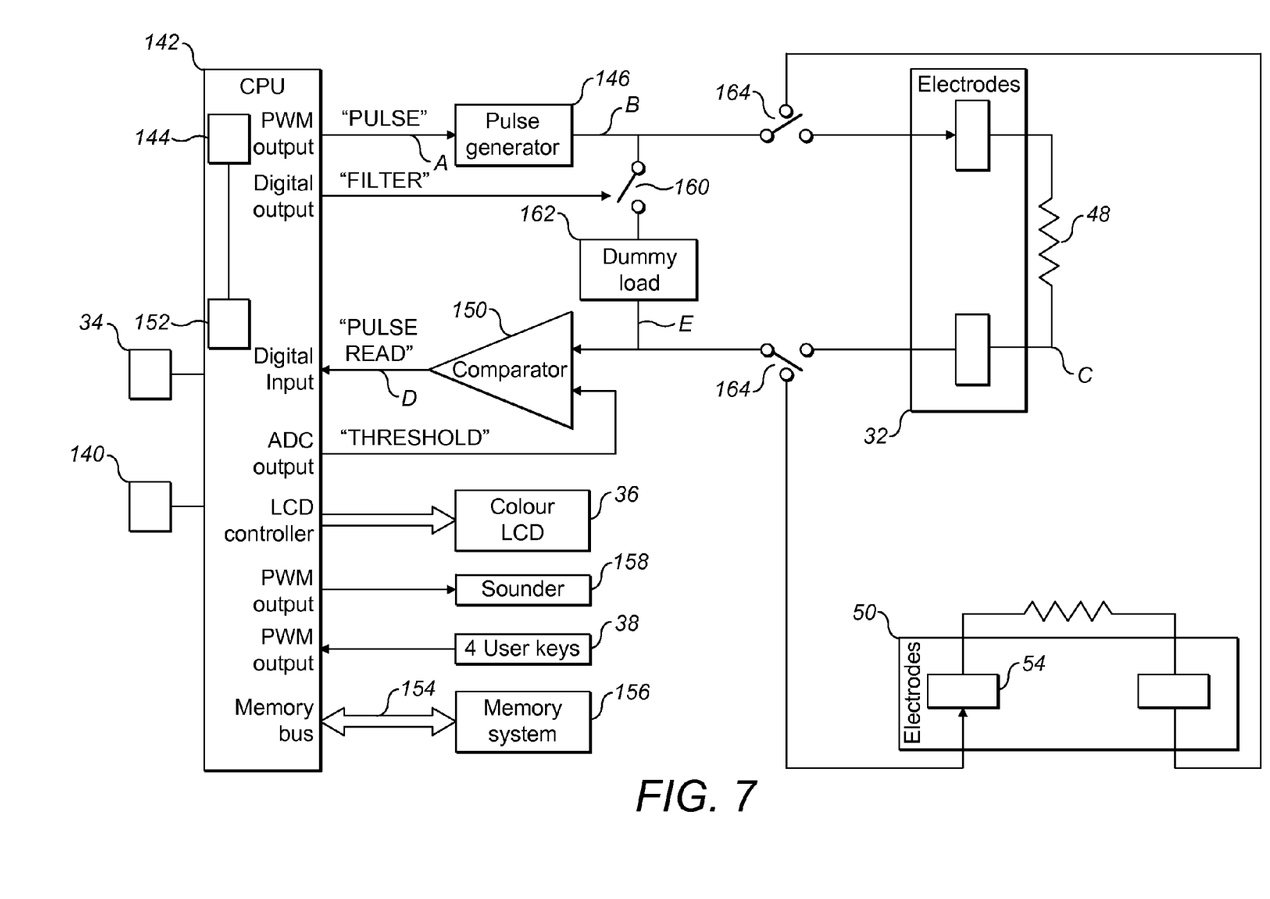
FIG. 7 is a block diagram of the circuitry within the treatment device of FIG. 1.

The electrical circuitry within the treatment device 10 for electro-stimulation of the body, either by means of the electrodes 32 or by means of the electrodes 54, is shown in FIG. 7 and is controlled by the on/off switch 34 and powered by a battery 140 for applying AC electrical impulses to the electrodes 32, 54. The standard arrangement for stimulating the electrodes 32 will be described first.

As shown, a central processing unit (CPU) 142 including a clock 144 is arranged to generate an output at point A of FIG. 7 in the form of a train of rectangular pulses. Such pulses are supplied to a waveform generator 146 for triggering an output from the generator at point B of the circuit. The output of the waveform generator 146 is an AC decaying oscillation, which is repeatedly triggered by the pulses from the CPU 142 and which is applied to one of the electrodes 32. A voltage signal is generated across the electrodes 32, effectively at point C in FIG. 7, whose magnitude is dependent on whether the electrodes are in open circuit or whether they are in contact with the skin and are responsive to the skin impedance (represented as a resistor 148). This voltage signal is applied to a comparator 150, where it is compared with a threshold voltage output by the CPU 142. The comparator 150 generates a pulse output at point D of the circuit, in which the rising edge of each pulse corresponds with the voltage from the electrodes 32 increasing above the threshold level and the trailing edge of each pulse corresponds with the voltage from the electrodes 32 falling below the threshold level. A counter 152 within the CPU 142 also connected to the clock 144 counts the clock signal for the duration of each such pulse and thereby produces a numerical value representing the pulse duration. These numerical values are transmitted by way of a memory bus 154 to a memory or store 156.

The user control keys 38 can be employed for providing inputs to the CPU 142 to cause the CPU 142 to adjust the frequency, duration, and amplitude of the pulses supplied to the waveform generator 146 and to determine whether these pulses are supplied at regular intervals, or repeatedly in clusters. The waveform generator 146 is arranged to respond accordingly for supplying a corresponding AC waveform to the electrodes 32, and in this way the electrical impulses applied to the skin can be adjusted and treatment can be controlled. The CPU 142 processes the information obtained during a treatment session and displays the results on the display 36 as well as storing them in the memory 156. The CPU 142 is also arranged to activate one or more audio indicators 158 for signalling certain events in the treatment session.

In addition, a series connection of a switch 160 and a load 162 is connected across the two electrodes 32 and may be switched into the circuit in response to a user generated output from the CPU 142, either in order to simulate skin contact when the electrodes 32 are not in contact with the skin of a patient or to provide a filter in cases of high skin sensitivity.

FIG. 7 also shows how the electrodes 54 of the treatment patch 50 according to the present invention may provide a parallel connection with the electrodes 32, wherein a switch arrangement 164 is arranged to switch between the electrodes 32 and the electrodes 54 according to whether the connection plug 58 of the treatment patch 50 is plugged into the socket 40 in the base of the treatment device 10. The action of plugging the connection plug 58 into the socket 40 is arranged to operate the switch 164 to disconnect the electrodes 32 and to connect the electrodes 54 into the electric circuit in their place. The purpose of this is explained further below.

The signals at the various points of the circuit of FIG. 7 and in various circumstances are shown in FIGS. 8 to 13.

Figure 8:
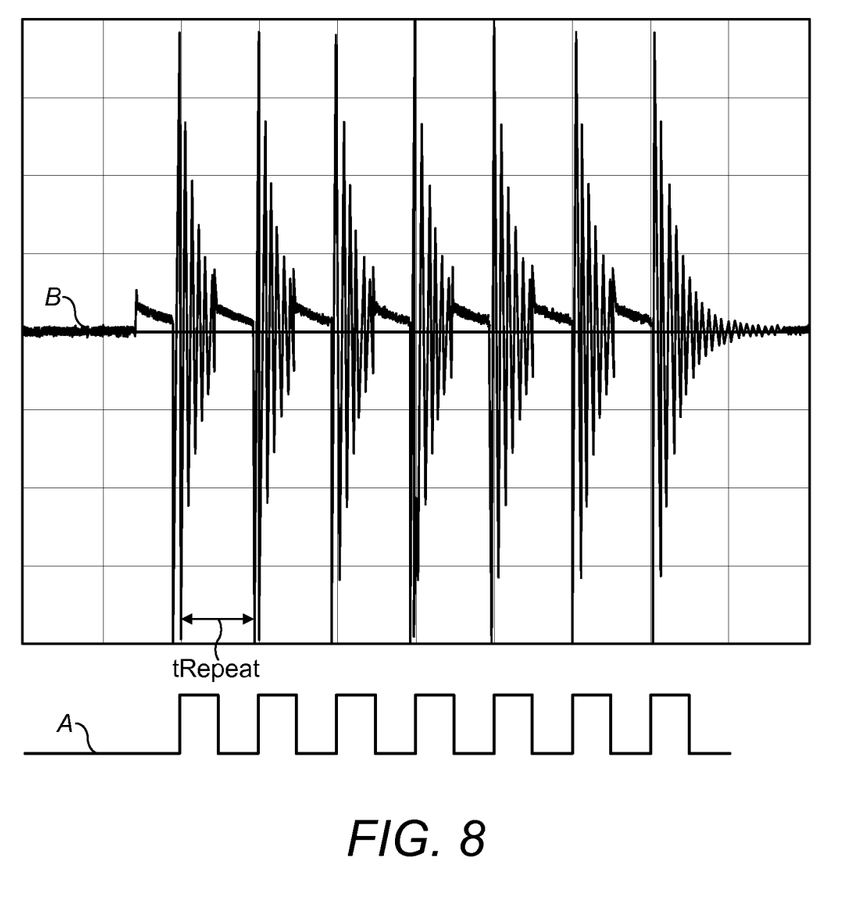
FIG. 8 is a waveform diagram showing an output of a waveform generator in the circuit of FIG. 7.
Figure 9:
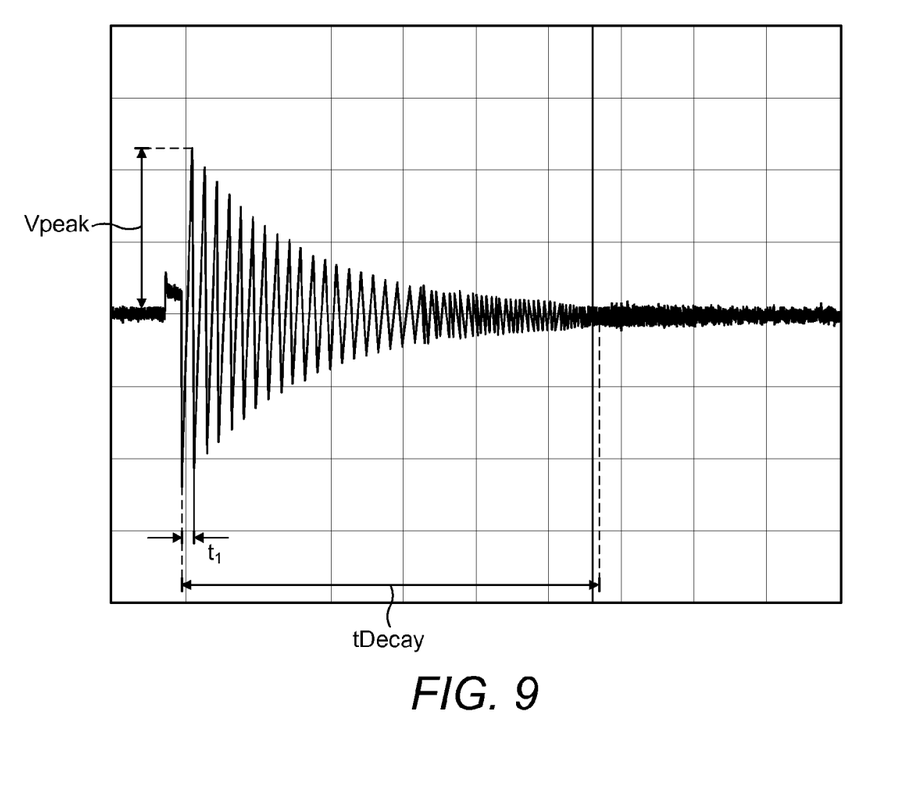
FIG. 9 is a waveform diagram showing a detail of the output of FIG. 8.

FIG. 8 shows the rectangular pulse signal output by the CPU 142 and generated at the point A of the circuit, together with the corresponding repeated AC waveform output by the waveform generator 146 at point B of the circuit. A single cycle of the AC waveform at point B is shown in FIG. 9, and has an initial amplitude $V_{peak}$, a half wavelength $t_1$ and a decay $t_{decay}$. The amplitude $V_{peak}$ represents signal strength and is dependent on the pulse width of the pulse signal at point A, which can be set by one of the control keys 38 according to a strength setting in a range from 1 to 250. In the example shown in FIG. 9, the strength setting is set to 20 and $V_{peak}$ is 230 volts. $t_1$ in this example is 40 microseconds and $t_{decay}$, to the point where the voltage has decayed to about 10% of $V_{peak}$, is 1.15 milliseconds.

The repetition rate of the AC waveform output by the waveform generator 146, as shown in FIG. 8, is determined by and corresponds with the frequency of the pulse signal at the point A and is set by the user from one of the control keys 38. The repetition rate is preferably adjustable from 50 Hz to 351 Hz. A further one of the control keys 38 sets whether the pulses output by the CPU 142 at the point A are generated at regular intervals or in clusters according to the intensity of the treatment required. The intensity of treatment can be set in a range from 1 to 8, representing the number of pulses, i.e. from 1 to 8, in each cluster. An intensity of 1 thus represents a series of pulses occurring at regular intervals, while an intensity of 8 represents clusters of 8 pulses at a time. The spacing between the individual pulses, or clusters of pulses, at the point A corresponds to the overall cycle time $t_{repeat}$ of each individual AC waveform, or cluster of waveforms, in the repeated cycle generated at the point B of the circuit and is also controlled by one of the user keys 38. This pulse spacing is defined as the gap in treatment applications, and the gap can be adjusted within the range from 10 to 80 corresponding to a spacing $t_{repeat}$ in a range from 220 microseconds to 1,600 microseconds.

By switching the load 162 into the circuit, the AC waveform output by the waveform generator 146 at the point B generates a waveform across the load 62 at the point E in FIG.

Figure 10:
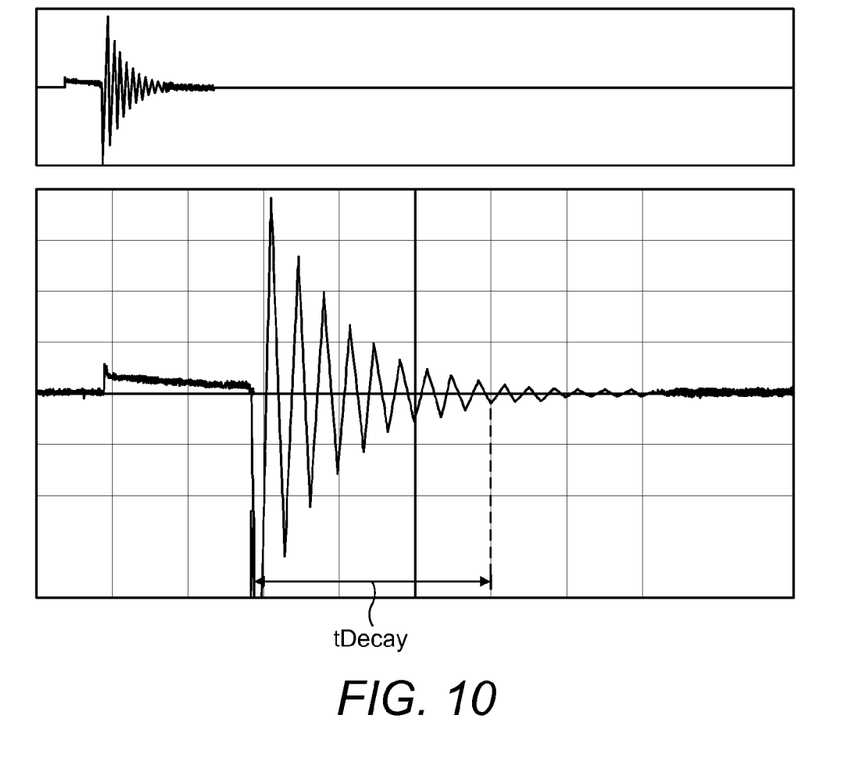
FIG. 10 is a waveform diagram showing the signal generated at one point of the circuit of FIG. 7 when the device is not in use but a load is connected across the electrodes to simulate skin contact.

7. The waveform at the point E is a modification of the signal at the point B, in which the half wavelength $t_1$ is extended, and is shown in FIG. 10.

By switching the treatment patch electrode 50 into the circuit, the AC waveform output by the waveform generator 146 at the point B generates a waveform across the electrodes 54 in exactly the same way as across the electrodes 32. The voltage signal generated across the electrodes 54 is effectively the same as that generated at point C in FIG. 7.

Having described the circuitry of the treatment device 10, in a situation where the device 10 is not in use, the application of electrical impulses through the electrodes 32 to the skin of a patient will now be described.

Figure 11:
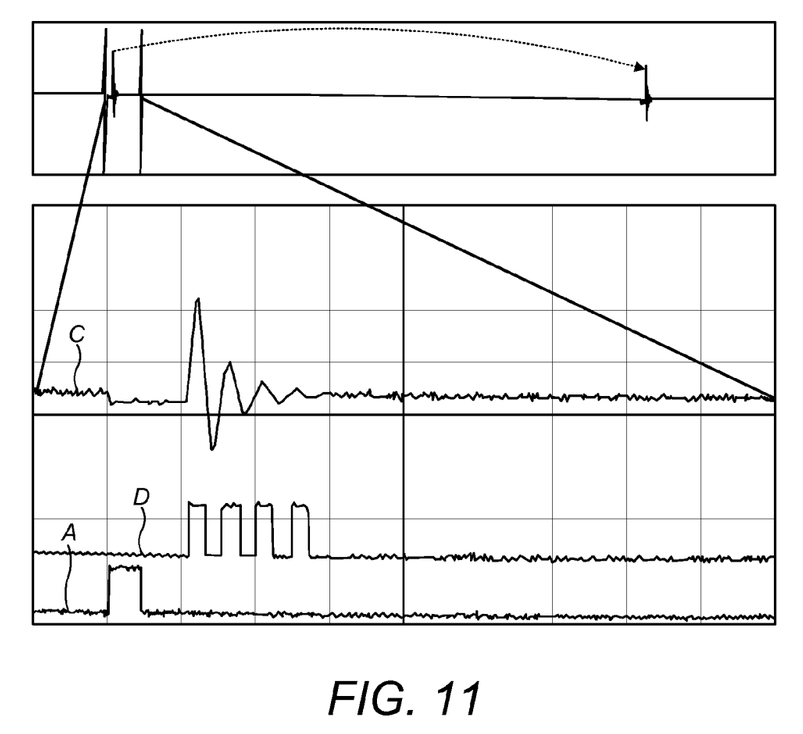
FIG. 11 is a signal diagram showing the signals generated at various points of the circuit of FIG. 7 when the treatment device is in use.

The signals described thus far effectively represent a situation where the electrodes 32 of the treatment device 10 are not in contact with the skin and where the device remains unaffected by skin impedance. The signals arising in use of the device are shown in FIG. 11, which represents the events triggered by one pulse from the pulse signal at the point A and hence one full cycle of the AC waveform at the point B. As shown, the effect of the skin impedance results in a signal generated at the point C of FIG. 7, which is an AC waveform having an extended half wavelength $t_1$ and a fewer number of voltage peaks by comparison with the AC waveform at the point B. This signal at the point C is supplied to the comparator 150 where it is compared with a threshold voltage $V_{th}$. On each occasion that the signal at the point C increases above the threshold voltage the comparator 150 triggers the leading edge of a new pulse, and on each occasion that the signal at the point C falls below the threshold $V_{th}$ the comparator generates the trailing edge of a pulse. The pulse output of the comparator 150 at the point D of FIG. 7 is shown in FIG. 11.

Figure 12:
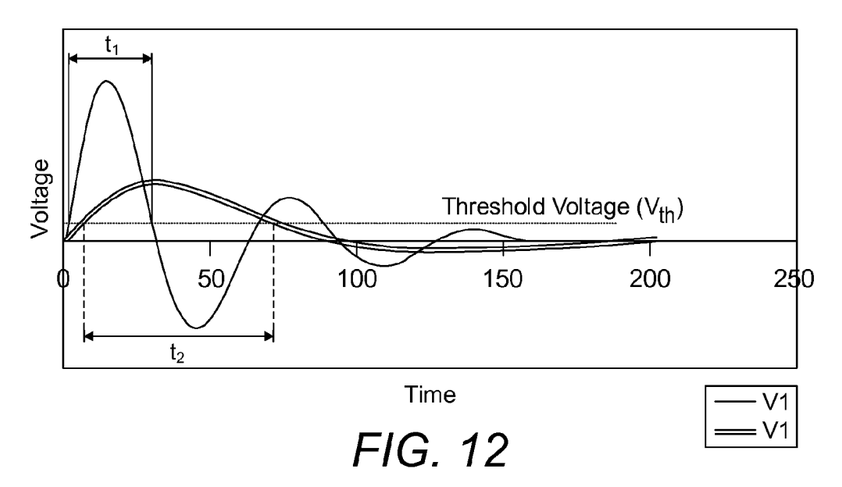
FIG. 12 is a waveform diagram showing how the signal at the electrodes of the treatment device varies in use as body surface impedance changes.

It has been found that, as treatment continues, the skin impedance falls and consequently the signal at the point C becomes increasingly extended. This is illustrated in FIG. 12 where an initial response signal at the point C is represented by the line $V_1$ having a half wavelength $t_1$, and a subsequent response signal at the point C is represented by the line $V_2$ having a half wavelength $t_2$. It is evident that $t_1$ is less than $t_2$. Eventually, the response signal at the point C will have a half wavelength $t_0$, in which the threshold voltage is not exceeded at all.

Figure 13:
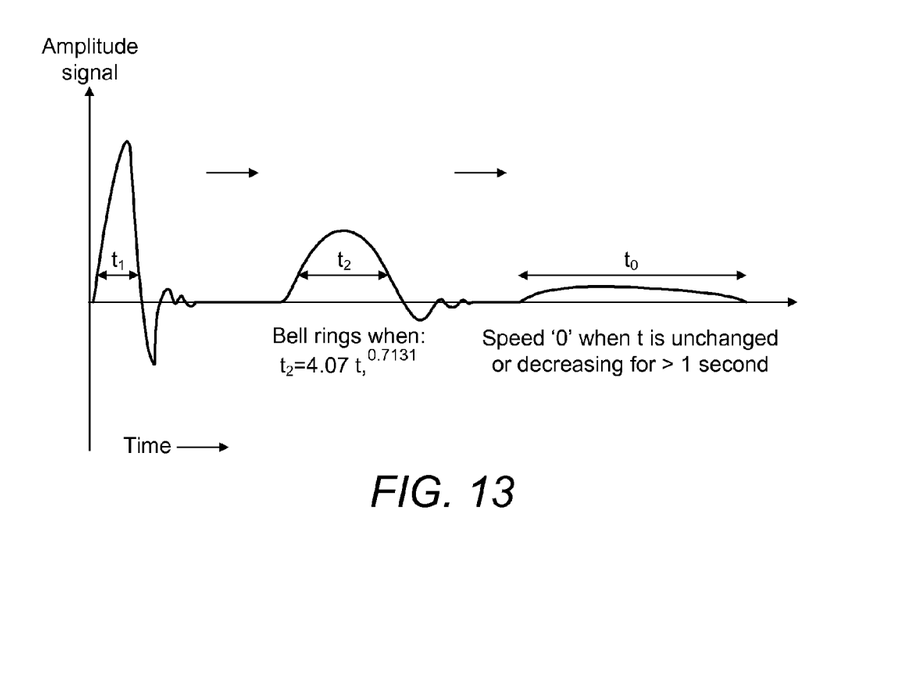
FIG. 13 is a waveform diagram corresponding to that of FIG. 12 and showing the waveform at the electrodes at three different time intervals.

This situation is represented in FIG. 13, which shows how the signal at the point C adapts as a treatment application progresses. Here, the initial skin impedance on first application of the AC waveform output by the waveform generator 146 at the point B is represented by the first signal in FIG. 13 and the half wavelength $t_1$; a subsequent application of the AC waveform at the point B is represented by the second signal in FIG. 13 and a half wavelength $t_2$; and a later application of the AC waveform at the point B is represented by the third signal and a half wavelength $t_0$.

Figure 14:
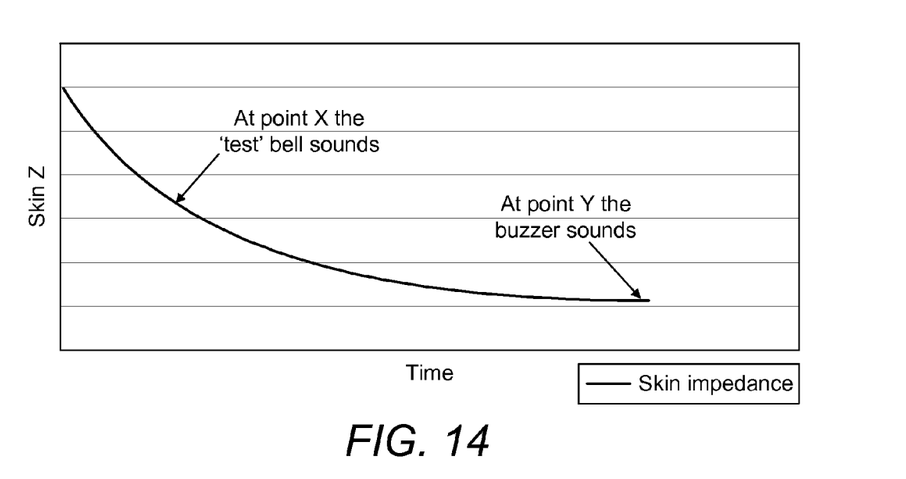
FIG. 14 is a graph representing the changes of body surface impedance with time.

The graph in FIG. 14 represents the change of skin impedance with time for one specific zone only of a given area of the body. By monitoring this change, the CPU 142 can deduce how the patient is responding to the application of the electrical impulses. The time that it takes to reach the point X on the graph represents the responsivity of the skin of this particular body zone. Point X might be selected empirically to be the point which satisfies the following equation:

$$t_2 = 4.087 t_1^{0.7131}$$

The point Y on the graph represents the point at which the rate of change of skin impedance Z with time t is zero, i.e.:

$$dZ/dt = 0$$

At the point Y, a standard treatment may be considered to have been administered. Referring back to FIG. 13, the second signal having the half wavelength $t_2$ corresponds to the point X in FIG. 14, and the third signal having the half wavelength $t_0$ corresponds to the point Y on the graph in FIG. 14.

In order to obtain a measurement corresponding to skin impedance, ideally the peak voltage values of each of the signals in FIG. 13 would be measured. However, it has been found more practical to measure the duration t of each initial half wave, and for this purpose the comparator 150 generates pulses in response to the crossings of the threshold voltage $V_{th}$ and the counter 152 counts to a numerical value determined in each instance by the generation of each pulse in the signal at the point D. These numerical count values are displayed on the display 36 of the device 10 under the control of the CPU 42.

Referring to FIG. 1, the initial reading for the count value corresponding to the half wavelength $t_1$ for the first signal in FIG. 13 occurring at the start of a treatment application is shown at the display location 36*a* at the top left hand corner of the display 36; the continually varying count value representing the half wavelength t as it changes during a treatment application is shown in the display location 36*b* in the lower left hand corner of the display 36, and a further count value representing the change of skin impedance with time, i.e. dZ/dt, and derived from counting the rate at which t changes by means of the counter 152 is displayed at the display location 36*c* on the display 36. At the moment when the point X is reached on the graph in FIG. 14, the CPU 142 is arranged to trigger the audio indicator 158 to ring a bell. At the same time, the CPU 42 stops the counter 152 and the count value at the display location 36*b* is fixed and is stored in the memory 156. At the moment at which the point Y on the graph in FIG. 14 is reached, as represented by the value at the display location 36*c* showing zero, the CPU 142 is arranged firstly to trigger the audio indicator 158 to sound a buzzer.

The most basic operation of the handheld treatment device 10 using the electrodes 32 will now be described, by way of example.

Firstly, the clinician switches the device on by means of the on/off switch 34 and sets the desired treatment strength and repetition rate by means of the control buttons 38. If desired, the clinician also sets the desired treatment intensity and treatment gap by means of the control buttons 38, and decides whether or not to apply the filter provided by the load 162 and, if so, sets this with a further control key 38.

Next, the clinician selects an area of the body for treatment and applies the electrical impulses to different body zones within this area. A number of initial readings will thus be generated and stored in the memory 156, and from the readings on the display location 36*a* the clinician will select a number of zones with relatively high initial readings, representing relatively high skin impedance, and will apply a treatment dose until the audio indicator 158 rings the bell. A new series of readings displayed at the display location 36*b* is thus generated and stored in the memory 156. The clinician now selects the highest of the readings in this second series of readings and applies a further set of electrical impulses until the audio indicator 158 sounds the buzzer. At this moment, a final reading is obtained as shown at the display location 36*b* corresponding to a zero at the display location 36*c,* and this final reading is also stored in the memory 156.

The above-description demonstrates use of the treatment device 10 for treating a variety of clinical conditions through the skin of a patient. However, in certain instances, access to the skin may not be available, for example following an accident involving a broken bone where it has been necessary to set the associated limb in a splint or a cast to ensure that movement does not irritate or exacerbate the fracture or inhibit a mend. In other circumstances, for example where the skin has been damaged, access may be prevented by a dressing, or alternatively repeated exposure for the purposes of treatment may irritate or exacerbate an already raw wound. Furthermore, the treatment device has hitherto been employed for electro-stimulation of the skin, and it has not been used in instances where the skin is seriously burned, damaged or missing.

In the present invention, it has been discovered that the electro-stimulation treatment may be applied to the body through areas of broken skin or directly through the raw surface of a wound, with beneficial healing effects and with only possibly certain adjustments to the electrical signals, as indicated below.

Therefore, in these circumstances, it is envisaged that the treatment patch electrode 50 according to the present invention may be employed in place of the electrodes 32 situated on the treatment head of the treatment device 10. Indeed, use of the treatment patch electrode 50 according to the invention has been found to be particularly useful in such circumstances.

The treatment patch electrode 50 may be applied to the surface of the body right at the outset of medical intervention and before any cast or wound dressing has been applied, and the patch elctrode may be left in place for the whole duration of the treatment, being connected up to the treatment device 10 on each occasion that electro-stimulation is to applied.

For these purposes, it is envisaged that a supply of treatment patch electrodes 50 of different sizes will be held in stock and a suitable one selected for the current treatment situation. Alternatively, a web of electrode material may be kept in stock and cut to a suitable size and thereafter fitted with leads 56 and a plug 58, which results in an even more versatile product.

A significant advantage of the treatment patch 50 according to the invention is that it is flexible and can be adapted to any portion of the body and will assume a contour that is curved to fit the body. Once the patch has been applied in the desired location, the fractured limb may be set in a plaster of paris cast, or a conventional wound dressing may be applied over the top of the patch 50, as required.

In practice, when the treatment patch 50 according to the invention is to be applied, the clinician will first use the treatment device 10 and the electrodes 32 to find the optimal point for application of the treatment patch 50. The clinician will interrogate the area around the wound or fracture and generally across the region to find potential body surface zones with relatively high initial readings, and will select one of these as the optimal zone for treatment. Paradoxically, the optimal region may not always be on the site of the fracture or the wound, and may even be on the opposite side of the body. However, the treatment patch 50 is obviously most significantly beneficially employed when the optimal zone is cited in the close vicinity of the fracture or wound.

Having located the optimal zone for electro-stimulation, the clinician employs the treatment device 10 with the electrodes 32 for determining the optimum signal strength and frequency for electro-stimulation.

Having located the zone for application of the treatment patch electrode 50 and determined the settings for treatment through the electrodes 32, the clinician now applies the treatment patch electrode 50 to the selected zone. The treatment device 50 is fixed in place, either by means of its own adhesive strip 76 or by the application of a conventional wound dressing over the patch electrode 50; or it is fixed in place and covered by a plaster of paris cast. In either instance, the connection plug 58 is left exposed for connection to the treatment device 10.

The clinician then connects the connection plug 58 of the treatment patch electrode 50 to the socket 40 of the treatment device 10. As already explained, this has the effect of switching the circuitry of FIG. 7 away from and disconnecting the electrodes 32 and connecting the electrodes 54 into the circuit in their place. At this point, the clinician may reduce the strength and frequency of the electrode stimulation using the buttons 38, particularly in the case of a wound which is likely to be damp and therefore more conductive than intact skin. The clinician then applies the initial electro-stimulation treatment, and afterwards disconnects the treatment patch electrode 50.

Thereafter, on each occasion that an electro-stimulation treatment is required for the duration of the therapeutic process, the clinician reconnects the treatment patch electrode 50 and conducts another electro-stimulation treatment until a satisfactory result has been effected.

As already indicated, various modifications to the described treatment patch electrode 50 are possible within the scope of the invention.

For example, the edge outlines of the electrode strips 54 may be varied, and instead of being formed from a band of joined rectangular or hexagonal shapes may be formed from straight line bands or parallel-sided zigzag line bands.

As mentioned, the electrodes may be formed as conductive coatings on an insulating backing, for example by electro-deposition, or they may be solid conductive strips separated by insulating film.

Preferably, the treatment patch electrode 50 is formed of biodegradeable material for ease of disposal, and it may be combined with its own cover layer for forming a wound dressing, or it may be provided separately and employed in conjunction with a conventional wound dressing.

Other modifications are also possible. For example, the comparator 150 for detecting feedback signals from the electrodes 32, 54 may be replaced by alternative detection means. Instead of measuring the duration of the pulses output by the comparator for detecting the time between crossings of the feedback waveform, detection means for measuring the peak value of the feedback waveform or the area between the feedback waveform and a threshold line may be employed.

Other possible variants include the replacement of the audio indicator 158 with a visual indicator and the replacement of the control buttons 38 with different control input means. The audio indicator may also be provided with a facility for issuing entertaining sounds, such as music, for use when children are being treated for keeping their interest alive.

The treatment patch electrode of the present invention has numerous significant advantages.

In particular, it has been found that the treatment patch electrode of the present invention as described above is capable of effectively treating a wide variety of illness and disease, as well as other clinical conditions. The patch electrode also has the advantages of being readily portable and disposable, as well as being easy to use and inexpensive to manufacture and produce.

The treatment patch electrode according to the present invention when employed in conjunction with the treatment device 10 significantly extends the range of applications for the treatment device 10. It has the advantage of flexibility, which ensures that it may conform closely to the contours of the patient's body parts, and thereby a maximum area of electrode interface and close proximity of the electrodes with the surface of the body is ensured for enhanced electro-stimulation treatment.

The simplicity of the treatment patch electrode 50 and its ease of application mean that it may be employed by suitably trained personnel having the skill to determine treatment settings, without requiring highly specialized medical practitioners to undertake the treatment.

The invention claimed is:

1. A handheld treatment device for applying electrical impulses to a living body through the surface of the body, for treating a variety of clinical conditions, comprising: first and second electrodes for contact with the skin; a waveform generator for repeatedly generating an AC waveform for applying electrical impulses through the electrodes to the skin; a detector for detecting changes in the skin impedance and for generating output signals representing the skin impedance; means responsive to the output signals from the detector for monitoring the responsivity of the skin; and indicator means for generating a first indication when a predetermined level of responsivity is reached and a second indication when a predetermined treatment has been administered;
    a treatment patch comprising:
    a flexible sheet having on one surface said first and second electrodes separated by insulation;
    a pair of leads connected respectively to said first and second electrodes; and
    a connection arrangement attached to the first and second leads for connecting the electrodes with said waveform generator;
    wherein each electrode comprises at least one elongate strip, and wherein the, or each, strip of the first electrode is separated from the, or each adjacent, strip of the second electrode by a, or a respective, line of said insulation.

2. A treatment device according, to claim 1 wherein each electrode strip is formed from one of:
    a linear band of conductive material;
    a zig zag band of conductive material;
    a band formed from joined rectangular or hexagonal elements of conductive material.

3. A treatment device according to claim 1 wherein the or each line of said insulation is of constant width.

4. A treatment device according to claim 1 wherein said first and second electrodes substantially cover and fill said one surface of said flexible sheet.

5. A treatment device according to claim 1 wherein said flexible sheet comprises a flexible hacking having conductive surface coatings providing said first and second electrodes.

6. A treatment device according to claim 5 wherein said flexible backing has an insulating coating providing, said insulation separating said first and second electrodes.

7. A treatment device according to claim 5 wherein said flexible backing is formed from insulating, material and at least one region of said flexible backing, is exposed between said first and second electrodes for providing said insulation.

8. A treatment device according to claim 1 further having a cover layer on said surface of said flexible sheet opposite said one surface.

9. A treatment device according to claim 8 wherein said cover layer has an adhesive edge strip surrounding said flexible sheet for affixing said treatment patch to the body of a patient.

10. A treatment device according to claim 1 wherein said flexible sheet is disposable.

11. A handheld treatment device for applying electrical impulses to a living body through the surface of the body, for treating a variety of clinical conditions, comprising: first and second electrodes for contact with the skin; a waveform generator for repeatedly generating an AC waveform for applying electrical impulses through the electrodes to the skin; a detector for detecting changes in the skin impedance and for generating output signals representing the skin impedance; means responsive to the output signals from the detector for monitoring the responsivity of the skin; and indicator means for generating a first indication when a predetermined level of responsivity is reached and a second indication when a predetermined treatment has been administered;
    a treatment patch comprising:
    a flexible sheet having on one surface said first and second electrodes separated by insulation;
    a pair of leads connected respectively to said first and second electrodes; and
    a connection arrangement attached to the first and second leads for connecting the electrodes with said waveform generator;
    wherein each electrode comprises a plurality of alternating elongate strips, and wherein each strip of the first electrode is separated from each adjacent strip of the second electrode by a respective line of said insulation.

* * * * *